US010993852B2

(12) United States Patent
Boll et al.

(10) Patent No.: US 10,993,852 B2
(45) Date of Patent: May 4, 2021

(54) ABSORBENT GARMENT WITH CLOSE FIT

(71) Applicant: Kimberly-Clark Worldwide, Inc., Neenah, WI (US)

(72) Inventors: Marie E. Boll, Appleton, WI (US); Kimberly Louise Ellefson, Oshkosh, WI (US); Ligia A. Rivera, Appleton, WI (US); Tammy J. Nettekoven, Neenah, WI (US); Kimberly M. Downs, Ripon, WI (US); Todd R. Hagner, Neenah, WI (US); Marlene R. Dins, Appleton, WI (US); Ronald Alex Hilt, Oshkosh, WI (US); Michael J. Kerins, Tucson, AZ (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 533 days.

(21) Appl. No.: 15/569,536

(22) PCT Filed: Apr. 29, 2015

(86) PCT No.: PCT/US2015/028202
§ 371 (c)(1),
(2) Date: Oct. 26, 2017

(87) PCT Pub. No.: WO2016/175780
PCT Pub. Date: Nov. 3, 2016

(65) Prior Publication Data
US 2018/0085263 A1 Mar. 29, 2018

(51) Int. Cl.
*A61F 13/496* (2006.01)
*A61F 13/53* (2006.01)
*A61F 13/49* (2006.01)

(52) U.S. Cl.
CPC ........ *A61F 13/4963* (2013.01); *A61F 13/496* (2013.01); *A61F 13/49019* (2013.01); *A61F 13/49061* (2013.01); *A61F 13/53* (2013.01); *A61F 2013/49068* (2013.01)

(58) Field of Classification Search
CPC ............ A61F 13/49061; A61F 13/4963; A61F 13/496; A61F 13/53; A61F 13/49019; A61F 2013/49068
See application file for complete search history.

(56) References Cited

U.S. PATENT DOCUMENTS

| 2,166,012 A | 7/1939 | La Maida |
| 2,252,992 A | 8/1941 | Steiner |
| 3,766,922 A | 10/1973 | Krusko |

(Continued)

FOREIGN PATENT DOCUMENTS

| BR | PI9905126 A | 10/2000 |
| CN | 102149355 A | 8/2011 |

(Continued)

*Primary Examiner* — Tatyana Zalukaeva
*Assistant Examiner* — Meagan Ngo
(74) *Attorney, Agent, or Firm* — Kimberly-Clark Worldwide, Inc.

(57) ABSTRACT

An absorbent garment has a minimum crotch width less than 30% the front region width. The absorbent garment has an absorbent member minimum width less than 80 mm. The absorbent member minimum width is less than 53% the minimum crotch width and is less than 60% the absorbent member maximum width.

3 Claims, 3 Drawing Sheets

(56) References Cited

U.S. PATENT DOCUMENTS

| | | |
|---|---|---|
| 3,807,402 A | 4/1974 | Duncan |
| 3,920,017 A | 11/1975 | Karami |
| 3,930,501 A | 1/1976 | Schaar |
| 4,037,602 A | 7/1977 | Hawthorne |
| 4,050,462 A | 9/1977 | Woon |
| 4,397,645 A | 8/1983 | Buell |
| 4,490,148 A | 12/1984 | Beckestrom |
| 4,500,316 A | 2/1985 | Damico |
| 4,610,681 A | 9/1986 | Strohbeen |
| 4,619,649 A | 10/1986 | Roberts |
| 4,753,646 A | 6/1988 | Enloe |
| 4,886,512 A | 12/1989 | Damico |
| 4,898,594 A | 2/1990 | Cottenden |
| 4,938,756 A | 7/1990 | Salek |
| 5,087,254 A | 2/1992 | Davis |
| 5,246,431 A | 9/1993 | Minetola |
| 5,462,537 A | 10/1995 | Carr |
| 5,582,606 A | 12/1996 | Bruemmer |
| 5,662,634 A | 9/1997 | Yamamoto |
| 5,672,166 A | 9/1997 | Vandemoortele |
| 5,895,382 A | 4/1999 | Popp |
| 5,931,823 A | 8/1999 | Stokes |
| 6,083,210 A | 7/2000 | Young |
| 6,240,569 B1 | 6/2001 | Van Gompel |
| 6,307,120 B1 | 10/2001 | Glaug |
| 6,514,233 B1 | 2/2003 | Glaug |
| 6,569,136 B1 | 5/2003 | Tao |
| 6,570,056 B1 | 5/2003 | Tanzer |
| 6,623,837 B2 | 9/2003 | Morman |
| 6,719,742 B1 | 4/2004 | McCormack |
| D492,409 S | 6/2004 | Otsubo |
| 6,793,650 B2 | 9/2004 | Weber |
| D498,298 S | 11/2004 | Otsubo |
| 6,891,080 B2 | 5/2005 | Minato |
| 6,972,011 B2 | 12/2005 | Maeda |
| D514,223 S | 1/2006 | Hermansson |
| D522,653 S | 6/2006 | Otsubo |
| 7,135,013 B2 | 11/2006 | Olson |
| D544,599 S | 6/2007 | Sasaki |
| 7,411,110 B2 | 8/2008 | Sawyer |
| 7,520,873 B2 | 4/2009 | Sosalla |
| 7,682,350 B2 | 3/2010 | Langdon |
| 7,803,244 B2 | 9/2010 | Siqueira |
| 7,824,389 B2 | 11/2010 | Veith |
| D629,890 S | 12/2010 | Hedbratt |
| 7,896,858 B2 | 3/2011 | Trennepohl |
| 8,017,827 B2 | 9/2011 | Hundorf |
| D650,477 S | 12/2011 | Morrell-Schwartz |
| 8,079,994 B2 | 12/2011 | Richlen |
| 8,105,303 B2 | 1/2012 | Sakaguchi |
| 8,226,624 B2 | 7/2012 | Hancock-Cooke et al. |
| 8,377,028 B2 | 2/2013 | Wheeler |
| 8,419,701 B2 | 4/2013 | McKiernan |
| 8,637,727 B2 | 1/2014 | Maldonado |
| 2001/0041876 A1 | 11/2001 | Creagan |
| 2002/0091368 A1 | 7/2002 | LaVon |
| 2002/0095129 A1 | 7/2002 | Friderich |
| 2003/0114814 A1 | 6/2003 | Baker |
| 2003/0114827 A1 | 6/2003 | Peterson |
| 2003/0130641 A1 | 7/2003 | Richlen |
| 2003/0171732 A1 | 9/2003 | Heyrman |
| 2003/0181883 A1* | 9/2003 | Olson ............... A61F 13/496 604/385.01 |
| 2004/0054342 A1 | 3/2004 | Newbill |
| 2004/0092897 A1 | 5/2004 | Macedo, Jr. |
| 2005/0010188 A1 | 1/2005 | Glaug |
| 2005/0027267 A1 | 2/2005 | Van Dyke |
| 2005/0124952 A1 | 6/2005 | Zehner |
| 2005/0148968 A1 | 7/2005 | Schlinz |
| 2005/0148975 A1 | 7/2005 | Van Gompel |
| 2005/0256493 A1 | 11/2005 | Datta |
| 2006/0064069 A1* | 3/2006 | Rajala ............... A61F 13/15601 604/385.24 |
| 2006/0149204 A1* | 7/2006 | Niemeyer ............... A61F 13/42 604/385.16 |
| 2006/0173428 A1 | 8/2006 | Acors |
| 2007/0123834 A1 | 5/2007 | McDowall |
| 2007/0233029 A1 | 10/2007 | Jansson |
| 2007/0287348 A1 | 12/2007 | Autran |
| 2008/0051747 A1 | 2/2008 | Cohen |
| 2008/0108967 A1 | 5/2008 | Mizushima |
| 2008/0132865 A1 | 6/2008 | Li |
| 2008/0132867 A1 | 6/2008 | Damaghi |
| 2008/0234643 A1 | 9/2008 | Kaneda |
| 2009/0182299 A1 | 7/2009 | Brinkdopke |
| 2009/0264851 A1* | 10/2009 | Richlen ............... A61F 13/5519 604/385.28 |
| 2010/0094236 A1 | 4/2010 | Schmitz |
| 2010/0108554 A1 | 5/2010 | Melius |
| 2011/0144602 A1 | 6/2011 | Long |
| 2011/0160687 A1 | 6/2011 | Welch |
| 2012/0016327 A1 | 1/2012 | Mason |
| 2012/0271267 A1 | 10/2012 | Love |
| 2012/0323204 A1 | 12/2012 | Poole |
| 2013/0006209 A1 | 1/2013 | Ruiz |
| 2013/0310798 A1 | 11/2013 | Glahn |
| 2014/0005623 A1 | 1/2014 | Wirtz |
| 2014/0018758 A1 | 1/2014 | Jayasinghe |
| 2014/0018764 A1* | 1/2014 | Johnston ............ A61F 13/49006 604/385.16 |
| 2014/0088538 A1* | 3/2014 | Borrero ............. A61F 13/49012 604/385.16 |
| 2014/0163501 A1* | 6/2014 | Ehrnsperger ........ A61F 13/4753 604/366 |
| 2014/0163502 A1 | 6/2014 | Arizti |
| 2014/0171898 A1 | 6/2014 | Greening, II |

FOREIGN PATENT DOCUMENTS

| | | |
|---|---|---|
| CN | 102281854 A | 12/2011 |
| CN | 102574389 A | 7/2012 |
| CN | 102844007 A | 12/2012 |
| CN | 102905665 A | 1/2013 |
| CN | 103458845 A | 12/2013 |
| CN | 103813768 A | 5/2014 |
| CN | 103857367 A | 6/2014 |
| EP | 0526225 A1 | 2/1993 |
| EP | 0858787 A1 | 9/1998 |
| EP | 0793469 B9 | 12/2002 |
| EP | 2253295 A1 | 11/2010 |
| EP | 2211812 B1 | 1/2012 |
| EP | 2144583 B1 | 5/2012 |
| JP | 2000175966 A2 | 6/2000 |
| JP | 2002238934 A2 | 8/2002 |
| JP | 2003070838 A2 | 3/2003 |
| JP | 2004208836 A2 | 7/2004 |
| JP | 2004528879 T2 | 9/2004 |
| JP | 2006042941 A2 | 2/2006 |
| JP | 2008220616 A2 | 9/2008 |
| JP | 2009521252 T2 | 6/2009 |
| JP | 4567670 B2 | 10/2010 |
| JP | 2011036280 A2 | 2/2011 |
| JP | 4912902 B2 | 4/2012 |
| JP | 5058271 B2 | 10/2012 |
| JP | 2013013683 A2 | 1/2013 |
| JP | 2013123447 A2 | 6/2013 |
| JP | 2013255564 A2 | 12/2013 |
| JP | 2014023949 A2 | 2/2014 |
| JP | 2015048546 A2 | 3/2015 |
| WO | 0002511 A1 | 1/2000 |
| WO | 11013736 A1 | 2/2011 |
| WO | 12053945 A1 | 4/2012 |
| WO | WO12054591 A1 | 4/2012 |
| WO | WO13172393 A1 | 11/2013 |
| WO | WO14002440 A1 | 1/2014 |

* cited by examiner

ABSORBENT GARMENT WITH CLOSE FIT

BACKGROUND OF THE INVENTION

Disposable absorbent garments are designed for absorbing body exudates and are similar in appearance, size, and shape to regular cloth underwear but are not designed to be laundered and reused. Many absorbent garments are designed to be pulled up around the user's body by utilizing stretchable materials that facilitate conformance to the anatomy of the user's torso like regular cloth underwear. However, the desire to make absorbent garments more like cloth underwear has to be balanced with the need to maintain product absorbency and performance. This balance is difficult on all product forms but is particularly pronounced with absorbent garments designed for use by adults because adequate amounts of absorbent material are initially needed at the crotch of the product near the point of insult. However, placement of excessive absorbent material at this location could have a negative effect on the comfort, fit, and discretion of the product. Thus, there remains a need for absorbent articles designed to fit a wide range of adult shapes and sizes that has a close and comfortable fit and yet provides the necessary leakage and absorbency performance expected by the user.

SUMMARY OF THE INVENTION

In one aspect, the present invention provides an absorbent garment defining a longitudinal direction and a transverse direction. The absorbent garment includes a front region defining a front edge, a first front side edge, and a second front side edge transversely opposed to the first front side edge. The front region also defines a front region width in the transverse direction between the first front side edge and the second front side edge.

The absorbent garment also includes a back region defining a back edge, a first back side edge, and a second back side edge transversely opposed to the first back side edge. The back region also defines a back region width in the transverse direction between the first back side edge and the second back side edge.

The absorbent garment also includes a crotch region disposed in the longitudinal direction between and interconnecting the front region and the back region. The crotch region defines a minimum crotch width. The minimum crotch width is less than 30% the front region width.

The absorbent garment also includes an absorbent member positioned in the crotch region and defining an absorbent member width measured transversely between an absorbent member first side edge and an absorbent member second side edge. The absorbent member width defines an absorbent member maximum width and an absorbent member minimum width. The absorbent member minimum width is less than 80 mm, the absorbent member minimum width is less than 60% the absorbent member maximum width, and the absorbent member minimum width is less than 53% the minimum crotch width.

In various embodiments of this aspect, the absorbent member minimum width is less than 65 mm. In various embodiments, the absorbent garment further defines a product length, as measured in the longitudinal direction between the front edge and the back edge, of at least 600 mm. In various embodiments, the absorbent member defines an absorbent capacity of at least 600 g saline.

In some embodiments, the absorbent garment further includes an intake layer defining a minimum width in the transverse direction between a first side edge and a second side edge. The intake layer minimum width is less than 85% the absorbent member minimum width.

In some embodiments, the absorbent garment is configured wherein the first front side edge is connected to the first back side edge at a first side seam and the second front side edge is connected to the second back side edge at a second side seam to form a pant-like configuration having a waist opening and two leg openings.

In some embodiments, the absorbent garment further includes a unitary laminate outer cover extending from the front edge to the back edge and extending from the first side seam to the second side seam.

In some embodiments, the absorbent garment further includes a first and a second containment flap extending in the longitudinal direction and being joined to a body-facing surface of the absorbent garment. Each of the first and the second containment flaps defines a height, measured from an attachment edge to a distal edge, of less than 20 mm. In these embodiments, the absorbent member minimum width may be less than 65 mm and each containment flap may have on off-set of at least 10 mm relative to the absorbent member minimum width.

In another aspect, the present invention provides an absorbent garment defining a longitudinal direction and a transverse direction. The absorbent garment includes a front panel, a back panel, and an insert panel. The front panel defines a front panel edge, a front panel crotch edge, a front panel first side edge, and a front panel second side edge transversely opposed to the front panel first side edge. The front panel also defines a front panel width in the transverse direction between the front panel first side edge and the front panel second side edge. The back panel defines a back panel edge, a back panel crotch edge, a back panel first side edge, and a back panel second side edge transversely opposed to the back panel first side edge. The back panel also defines a back panel width in the transverse direction between the back panel first side edge and the back panel second side edge. The insert panel is disposed longitudinally between and interconnects the front panel and the back panel. The insert panel defines an insert panel width measured in the transverse direction between an insert panel first side edge and an insert panel second side edge. The insert panel width has a maximum and a minimum. The insert panel includes a body-facing liner, a garment-facing back sheet, and an absorbent member positioned between the liner and the back sheet. The absorbent member extends in the longitudinal direction from the front panel to the back panel. The absorbent member defines an absorbent member width measured in the transverse direction between an absorbent member first side edge and an absorbent member second side edge. The absorbent member width has a maximum and a minimum. The absorbent member minimum width is less than 80 mm and the absorbent member minimum width is less than 53% the insert panel minimum width. The absorbent member minimum width is less than 60% the absorbent member maximum width. The front panel first side edge is connected to the back panel first side edge at a first side seam and the front panel second side edge is connected to the back panel second side edge at a second side seam to form a pant-like configuration having a waist opening and two leg openings.

In various embodiments of this aspect, the insert panel minimum width is less than 30% the front panel width. In various embodiments of this aspect, the absorbent garment includes a first and a second containment flap extending in the longitudinal direction from an insert panel front edge to an insert panel back edge. The first and the second containment flaps terminate at the insert panel front edge and terminate at the insert panel back edge. Each of the first and the second containment flaps define a height, measured from an attachment edge to a distal edge, of less than 20 mm. The absorbent member minimum width is less than 65 mm.

In various embodiments of this aspect, the absorbent garment further includes an intake layer having a minimum width in the transverse direction between a first side edge and a second side edge. The intake layer minimum width is less than 85% the absorbent member minimum width.

In another aspect, the present invention provides an absorbent garment defining a longitudinal direction and a transverse direction. The absorbent garment includes a front region defining a front edge, a first front side edge, and a second front side edge transversely opposed to the first front side edge, wherein the front region defines a front region width in the transverse direction between the first front side edge and the second front side edge. The absorbent garment includes a back region defining a back edge, a first back side edge, and a second back side edge transversely opposed to the first back side edge, wherein the back region defines a back region width in the transverse direction between the first back side edge and the second back side edge. The absorbent garment defines a product length, as measured in the longitudinal direction between the front edge and the back edge, of at least 600 mm. The absorbent garment also includes a crotch region disposed in the longitudinal direction between and interconnecting the front region and the back region. The crotch region defines a minimum crotch width, wherein the minimum crotch width is less than 30% the front region width. The absorbent article also includes an absorbent member positioned in the crotch region and extending longitudinally from the front region to the back region. The absorbent member defines an absorbent member width measured transversely between an absorbent member first side edge and an absorbent member second side edge. The absorbent member width defines an absorbent member maximum width and an absorbent member minimum width, wherein the absorbent member minimum width is less than 80 mm, the absorbent member minimum width is less than 60% the absorbent member maximum width, the absorbent member minimum width is less than 53% the minimum crotch width, and the absorbent garment defines an absorbent capacity of at least 600 g. The absorbent garment is configured such that the first front side edge is connected to the first back side edge at a first side seam and the second front side edge is connected to the second back side edge at a second side seam to form a pant-like configuration having a waist opening and two leg openings.

In various embodiments of this aspect, the absorbent garment further includes a unitary outer cover extending from the front edge to the back edge in the longitudinal direction and extending from the first side seam to the second side seam in the transverse direction.

In various embodiments of this aspect, the front region includes a front panel defining a front panel crotch edge. The front panel extends from the front edge to the front panel crotch edge in the longitudinal direction and extends from the first front side edge to the second front side edge in the transverse direction to define a front panel area. The front panel includes a laminate of two nonwoven layers superposed on opposing surfaces of a polymeric film layer, wherein the two nonwoven layers and the polymeric film layer extend substantially through the entire front panel area. The back region includes a back panel defining a back panel crotch edge. The back panel extends from the back edge to the back panel crotch edge in the longitudinal direction and extends from the first back side edge to the second back side edge in the transverse direction to define a back panel area. The back panel includes a laminate of two nonwoven layers superposed on opposing surfaces of a polymeric film layer, wherein the two nonwoven layers and the polymeric film layer extend substantially through the entire back panel area. The crotch region includes an insert panel disposed longitudinally between and interconnecting the front panel and the back panel.

In some embodiments of this aspect, the insert panel includes the absorbent member positioned between a liquid-permeable body-facing liner and a liquid-impermeable garment-facing back sheet.

In some embodiments of this aspect, the absorbent garment further includes a first and a second containment flap extending in the longitudinal direction and being joined to a body-facing surface of the absorbent garment. Each of the first and the second containment flaps defines a height, measured from an attachment edge to a distal edge, of less than 20 mm. In some embodiments, the absorbent member minimum width is less than 65 mm and each of the first and the second containment flaps has on off-set of at least 10 mm relative to the absorbent member minimum width.

In some embodiments of this aspect, the absorbent garment further includes an intake layer having a minimum width in the transverse direction between a first side edge and a second side edge. The intake layer minimum width is less than 85% the absorbent member minimum width.

DETAILED DESCRIPTION OF THE DRAWINGS

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

The terms "disposed on," "disposed along," "disposed with," or "disposed toward" and variations thereof are intended to mean that one element can be integral with another element, or that one element can be a separate structure bonded to or placed with or placed near another element.

"Fiber" refers to a continuous or discontinuous member having a high ratio of length to diameter or width. Thus, a fiber may be a filament, a thread, a strand, a yarn, or any other member or combination of these members.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons, et al. Meltblown fibers may be continuous or discontinuous and are generally self bonding when deposited onto a collecting surface.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

These terms may be defined with additional language elsewhere in the specification.

References to FIGS. 1 to 5 shall be made in describing various aspects and embodiments of the invention. It should be noted that the embodiments depicted in FIGS. 1-5 are merely representative examples of the garment (or portions of a garment) of the invention. Although for illustrative purposes certain features of the present invention shall be described and illustrated with respect to an adult incontinence garment, the various aspects and embodiments of the present invention are also suitable for use with diapers, swim pants, training pants, enuresis garments, menstrual pants, and the like.

Figure 1:
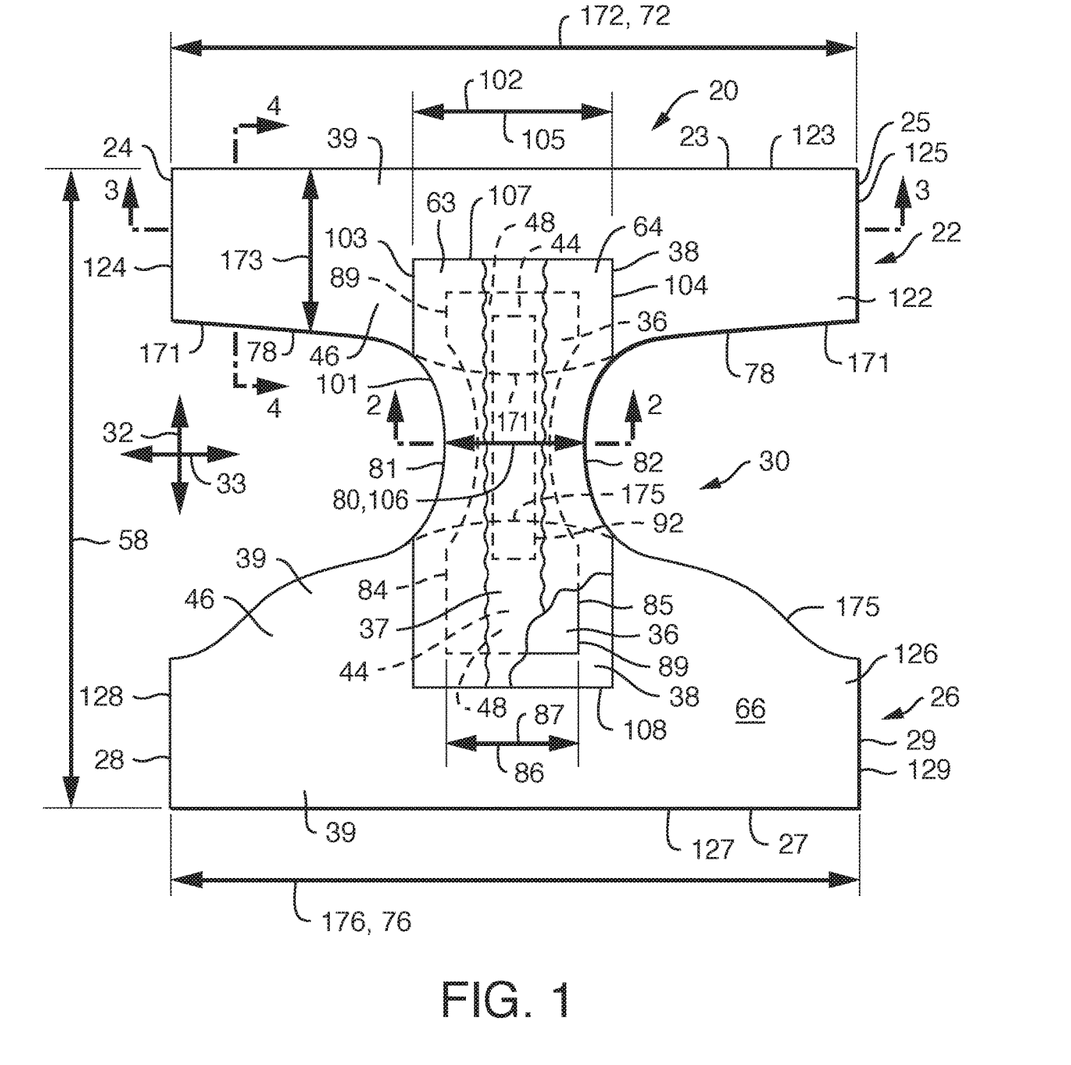
FIG. 1 representatively illustrates a plan view of one embodiment of an absorbent garment incorporating the principles of the present invention in a longitudinally and transversely stretched and laid-flat condition with portions cut away to show underlying features. The absorbent garment is shown prior to the joining of the front and back waist regions with the surface of the garment that faces the wearer when the garment is worn facing the viewer.
Figure 2:
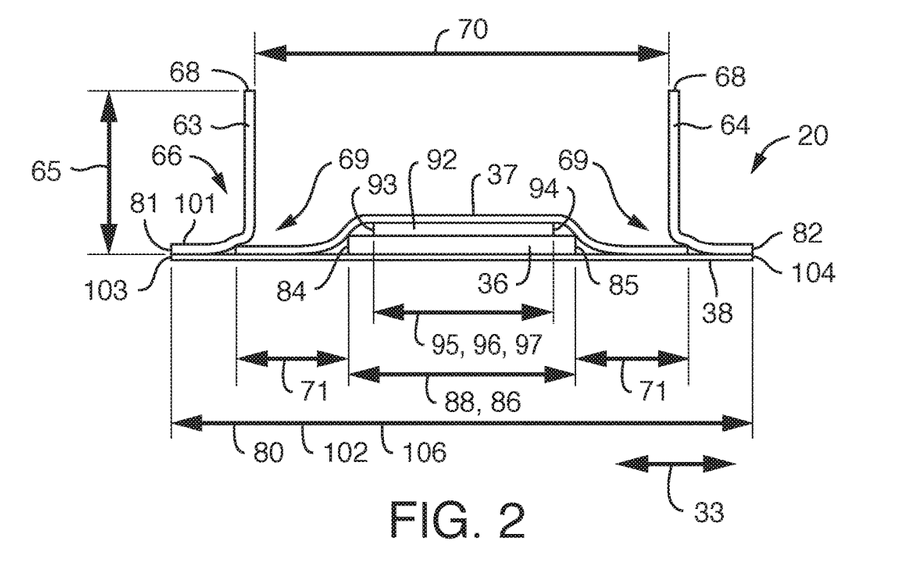
FIG. 2 representatively illustrates a cross-sectional view of FIG. 1 taken along line 2-2.
Figure 3:
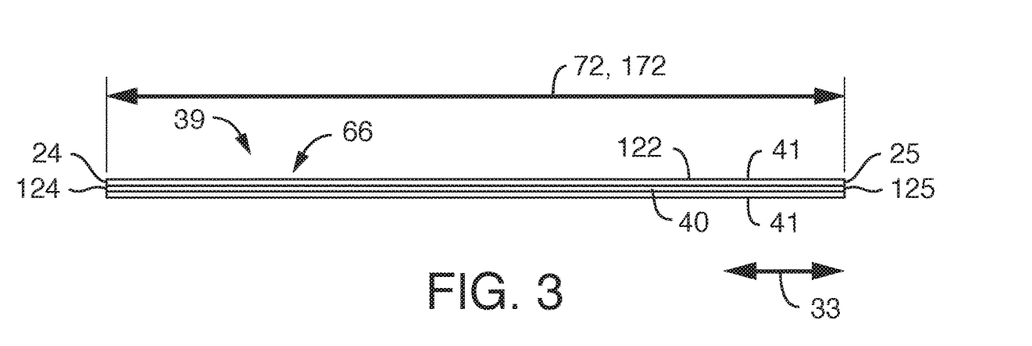
FIG. 3 representatively illustrates a cross-sectional view of FIG. 1 taken along line 3-3.
Figure 4:
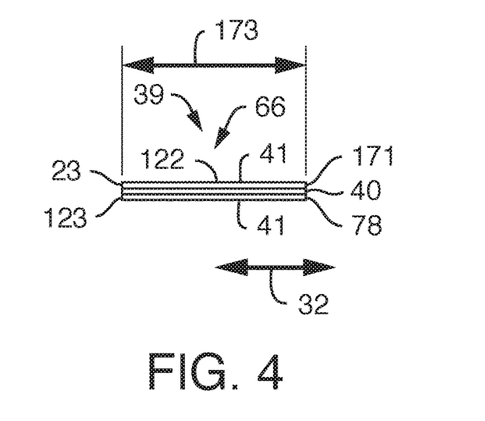
FIG. 4 representatively illustrates a cross-sectional view of FIG. 1 taken along line 4-4.
Figure 5:
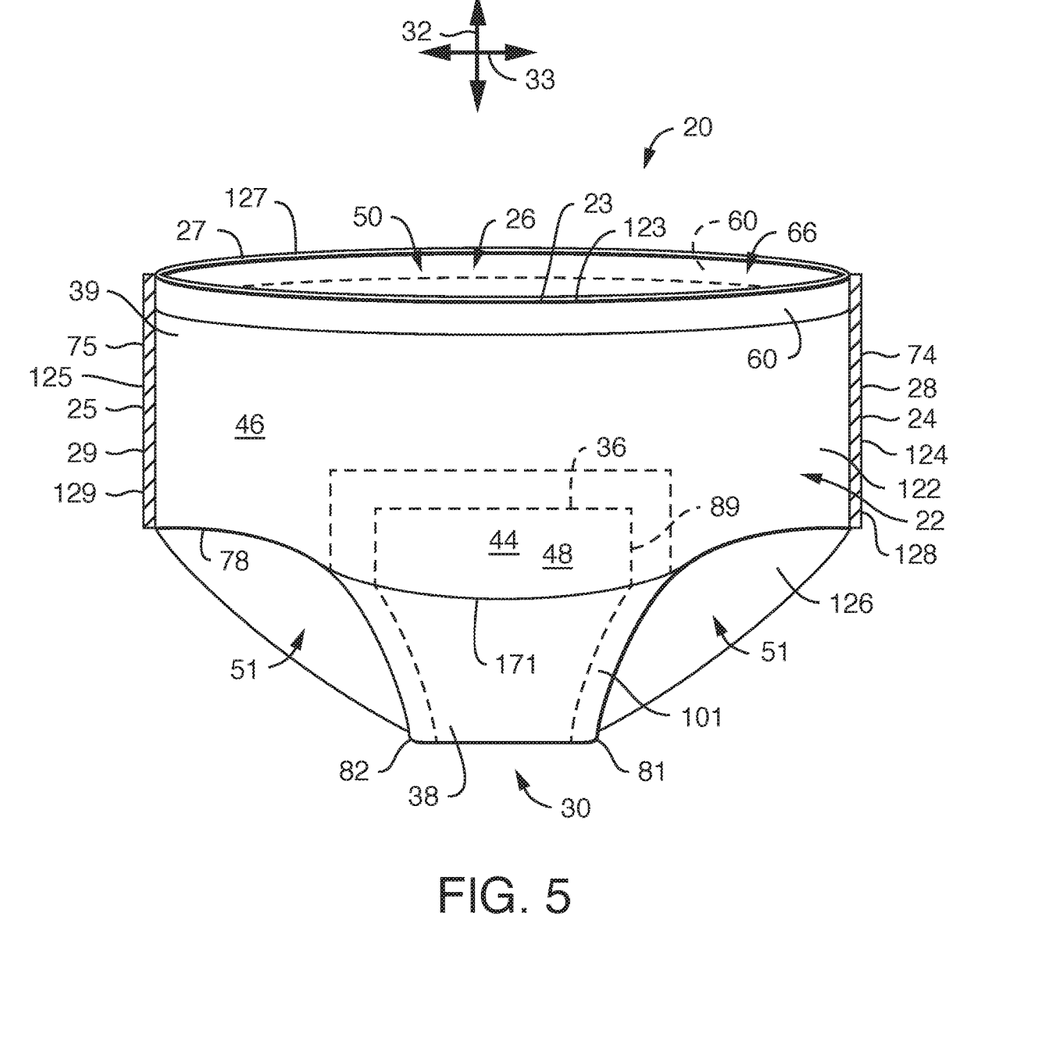
FIG. 5 representatively illustrates a front perspective view of the embodiment of FIG. 1, with the front and back waist regions being joined such that the garment is in a pull-on, pant-like configuration.

Referring to FIG. 1, a plan view of one embodiment of an absorbent garment 20 is representatively illustrated in a longitudinally and transversely stretched and laid-flat condition with portions cut away to show underlying features and with the body-facing surface of the absorbent garment facing the viewer. The absorbent garment 20 is illustrated in a condition prior to the joining of the front and back waist regions. The absorbent garment 20 defines a longitudinal direction 32 and a transverse direction 33 which is perpendicular to the longitudinal direction 32. The absorbent garment 20 includes a front region 22, a back region 26, and a crotch region 30. Other views of the absorbent garment 20 of FIG. 1 are also seen in FIGS. 2, 3, and 4. FIG. 2 representatively illustrates a cross-sectional view of FIG. 1 taken along line 2-2. FIG. 3 representatively illustrates a cross-sectional view of FIG. 1 taken along line 3-3. FIG. 4 representatively illustrates a cross-sectional view of FIG. 1 taken along line 4-4. FIG. 5 representatively illustrates a front perspective view of the embodiment of FIG. 1, with the front and back waist regions being joined such that the garment is in a pull-on, pant-like configuration.

The front region 22 defines a front edge 23, a first front side edge 24, and a second front side edge 25 transversely opposed to the first front side edge 24. The front region 22 defines a front region width 72 measured in the transverse direction 33 between the first front side edge 24 and the second front side edge 25 as illustrated in FIGS. 1 and 3. The front region width 72 is measured with the absorbent garment 20 fully extended in the transverse direction 33. As used herein, the term "fully extended" describes the condition wherein the garment is extended in a given direction to the point where any further extension in said direction would result in one or more material failures (e.g., rupture or permanent deformation). In embodiments wherein the first front side edge and/or the second front side edge are non-parallel with the longitudinal direction (not illustrated), the front region width is the maximum width measured parallel with the transverse direction from any point on the first front side edge to any point on the second front side edge. In various embodiments, the front region width 72 may be 600 to 1000 mm, 700 to 900 mm, or 750 to 850 mm. In some embodiments the front region width 72 may be about 750 mm or about 840 mm. The back region 26 defines a back edge 27, a first back side edge 28, and a second back side edge 29 transversely opposed to the first back side edge 28. The back region 26 defines a back region width 76 measured in the transverse direction 33 between the first back side edge 28 and the second back side edge 29 as illustrated in FIG. 1. The back region width 76 is measured with the absorbent garment 20 fully extended in the transverse direction 33. In embodiments wherein the first back side edge and/or the second back side edge are non-parallel with the longitudinal direction (not illustrated), the back region width is the maximum width measured parallel with the transverse direction from any point on the first back side edge to any point on the second back side edge. In various embodiments, the back region width 76 may be 600 to 1000 mm, 700 to 900 mm, or 750 to 850 mm. In some embodiments the back region width 76 may be about 750 mm or about 840 mm. The absorbent garment 20 further defines a product length 58 as measured in the longitudinal direction 32 from the front edge 23 to the back edge 27 as illustrated in FIG. 1. The product length 58 is measured with the absorbent garment 20 fully extended in the longitudinal direction 32. In various embodiments, the product length 58 may be at least 600 mm, at least 650 mm, or at least 700 mm.

In particular embodiments, and as representatively illustrated in FIG. 5, the first front side edge 24 may be connected to the first back side edge 28 at a first side seam 74 and the second front side edge 25 may be connected to the second back side edge 29 at a second side seam 75, such that the garment defines a pull-on, pant-like configuration having a waist opening 50 and two leg openings 51.

The crotch region 30 is disposed in the longitudinal direction 32 between and interconnecting the front region 22 and the back region 26. The crotch region defines a crotch region width in the transverse direction 33 between a first crotch side edge 81 and a second crotch side edge 82. The crotch region width is measured with the absorbent garment in a fully extended and laid flat condition. The crotch region width includes a minimum crotch width 80 as illustrated in FIG. 2. In various embodiments, the minimum crotch width 80 is less than 20%, less than 25%, or less than 30% the front region width 72. In some embodiments, minimum crotch width 80 may be about 150 mm and the front region width 72 may be about 750 mm or about 840 mm. In other embodiments, the minimum crotch width 80 may be about 210 mm and the front region width 72 may be about 750 mm or about 840 mm. The lower the percentage the minimum crotch width, relative to the front region width, the more shaped the absorbent garment is. In other words, the higher the percentage (up to 100%) the more rectangular the absorbent garment. In various embodiments, the minimum crotch width 80 is located proximate the longitudinal centerline of the absorbent garment 20 as illustrated in FIG. 1 and is less than 30% the front region width 72.

The crotch region 30 also includes an absorbent member 36 that may extend in the longitudinal direction 32 from the front region 22, through the crotch region 30, and to the back region 26. In various embodiments, the absorbent member may extend only from the crotch region to the front region, only from the crotch region to the back region, or may be positioned only within the crotch region (not illustrated). The absorbent member 36 defines an absorbent member width 86 measured in the transverse direction 33 between an absorbent member first side edge 84 and an absorbent member second side edge 85 as illustrated in FIGS. 1 and 2. The absorbent member width 86 defines an absorbent member maximum width 87 (FIG. 1) and an absorbent member minimum width 88 (FIG. 2). In various embodiments, the absorbent member minimum width 88 is less than 80 mm, less than 75 mm, less than 70 mm, or less than 65 mm. In various embodiments, the absorbent member minimum width 88 is less than 70%, less than 65%, less than 60%, less than 55%, less than 50%, or less than 45% the absorbent member maximum width 87. In some embodiments, the absorbent member minimum width 88 is about 41% the absorbent member maximum width 87. The lower the percentage the absorbent member minimum width, relative to the absorbent member maximum width, the more shaped the absorbent member is. In other words, the higher the percentage (up to 100%) the more rectangular the absorbent member. In the present invention, it has been found that the overall absorbent capacity of the absorbent garment can be maintained with an absorbent member having a narrower crotch, without increasing the thickness of the absorbent member, by moving some of the absorbent material to the laterally extending ear portions 89 of the absorbent member 36 as illustrated in FIGS. 1 and 5. In various embodiments, the absorbent member minimum width 88 is located proximate the longitudinal centerline of the absorbent member. In some embodiments, the absorbent member minimum width 88 is located in the crotch region 30 of the absorbent garment 20 and the absorbent member maximum width 87 is located in the front region 22 or the back region 26. In some embodiments, the absorbent member maximum width 87 is located in both the front region 22 and the back region 26 as illustrated in FIG. 1.

In some embodiments, the absorbent member minimum width 88 is less than 53% the minimum crotch width 80. The relatively wider crotch width provides for greater contained volume surrounding the absorbent member at its narrowest point. This increased volume is believed to allow space for the urine to reside until it can be absorbed by the absorbent member. This increased volume is also believed to provide additional containment space for the male anatomy while still providing a close fitting garment.

The absorbent member can be constructed of materials known in the art as suitable for absorbing liquid excretions, such as wood pulp fluff, superabsorbent polymers, absorbent foam, and the like. The absorbent member is, in particular embodiments, encased in one or more substrates. For example, the absorbent member could be wrapped in a tissue and/or a nonwoven substrate. Alternatively, or in addition, the absorbent member can be sandwiched between a garment-side, liquid impermeable back sheet and a body-side, liquid permeable liner. For example, the crotch region 30 can include an absorbent member 36 sandwiched between a liner 37 and a back sheet 38, as representatively illustrated in FIGS. 1 and 2. The absorbent member width 86 does not include any optional liners, back sheets, tissues, or wraps.

In various embodiments, the absorbent garment may have any suitable absorbent capacity. In some embodiments, the absorbent garment may have an absorbent capacity of 300 to 1000 g saline, 350-800 g saline, or 350-700 g saline. In some embodiments, the absorbent garment has an absorbent capacity of at least 300, 400, 500, or 600 g saline. In particular embodiments, the absorbent capacity may be about 350 g saline or about 700 g saline.

In some embodiments, the absorbent garment may further include an optional intake layer 92 as illustrated in FIGS. 1 and 2. The intake layer 92 may be adapted to work in conjunction with the absorbent member 36. In particular, the intake layer 92 may have a higher void volume than the absorbent member 36 to quickly intake and hold fluids so the absorbent member 36 has time to absorb the fluid without leaking. The intake layer 92 defines an intake layer width 95 measured in the transverse direction 33 between an intake layer first side edge 93 and an intake layer second side edge 94. The intake layer width 95 includes an intake layer maximum width 96 and an intake layer minimum width 97. In some embodiments, the intake layer minimum width 97 is less than 85% the absorbent member minimum width 88. In other embodiments, the intake layer minimum width 97 may be 90-100% the absorbent member minimum width 88.

In particular embodiments, the front region 22 may be constructed, at least in part, of a laminate 39 that comprises a polymeric film layer 40 and at least one nonwoven layer 41, wherein both the polymeric film layer 40 and the nonwoven layer 41 extend substantially throughout the entire area of the laminate 39. In other embodiments, the front region 22 may be constructed, at least in part, of a laminate that comprises elastomeric strands and at least one nonwoven layer wherein the elastomeric strands and the nonwoven layer extend substantially throughout the entire area of the laminate (not illustrated).

In one embodiment, representatively illustrated in FIGS. 3 and 4, the laminate 39 comprises two nonwoven layers 41/41 superposed on opposing top and bottom surfaces of the polymeric film 40 such that the polymeric film 40 is sandwiched between the two nonwoven facings 41/41, and both the polymeric film 40 and both nonwoven layers 41/41 extend substantially through the entire area of the laminate 39. In particular embodiments, as representatively illustrated in FIG. 3, the laminate 39 transversely extends from the first front side edge 24 to the second front side edge 25. In another embodiment (not illustrated), the laminate may include two nonwoven layers superposed on opposing top and bottom surfaces of a plurality of elastomeric strands such that the polymeric strands are sandwiched between the two nonwoven facings, and the elastomeric strands and the nonwoven layers extend substantially through the entire area of the laminate. In particular embodiments, the laminate with elastomeric strands may extend from the first front side edge to the second front side edge.

In particular embodiments, as representatively illustrated in FIG. 4, the laminate 39 longitudinally extends from the front edge 23 to a front leg edge 78. In another embodiment (not illustrated), the laminate may include two nonwoven layers superposed on opposing top and bottom surfaces of a plurality of elastomeric strands such that the polymeric strands are sandwiched between the two nonwoven facings, and the elastomeric strands and the nonwoven layers extend substantially through the entire area of the laminate. In particular embodiments, the laminate with elastomeric strands may extend from the front edge to the front leg edge.

In particular embodiments, both the front region and the back region can comprise a laminate and the laminate can, but need not, extend from the front region to the back region, such that the laminate is continuous and integral through the front region, crotch region, and back region and extends from the front edge to the back edge and from the first side seam to the second side seam (not illustrated). In other words, the laminate may be unitary throughout the absorbent garment. In other embodiments, a unitary outer cover may extend from the front region to the back region, such that the outer cover is continuous and integral through the front region, the crotch region, and the back region and extends from the front edge to the back edge and from the first side seam to the second side seam (not illustrated). In these embodiments, the unitary outer cover may or may not be elastomeric.

In some embodiments, as representatively illustrated in FIGS. 1, 2, and 5, the front region 22, may be defined, at least in part, by a front panel 122. The front panel 122 may be a laminate like any of those described herein. For example, the front panel 122 may comprise a laminate of two nonwoven layers superposed on opposing surfaces of a polymeric film layer. In some embodiments, the two nonwoven layers and the polymeric film layer extend substantially through the entire area of the front panel 122. The front panel 122 defines a front panel edge 123, a front panel crotch edge 171, a front panel first side edge 124, and a front panel second side edge 125. The front panel first side edge 124 is opposed to the front panel second side edge 125 in the transverse direction 33. The front panel 122 defines a front panel width 172 measured, with the garment fully extended, in the transverse direction 33 between the front panel first side edge 124 and the front panel second side edge 125. The front panel 122 also defines a front panel length 173 measured, with the garment fully extended, in the longitudinal direction 32 between the front panel edge 123 and the front panel crotch edge 171.

Likewise, the back region 26, may be defined, at least in part, by a back panel 126. The back panel 126 may be a laminate like any of those described herein. For example, the back panel 126 may comprise a laminate of two nonwoven layers superposed on opposing surfaces of a polymeric film layer. In some embodiments, the two nonwoven layers and the polymeric film layer extend substantially through the entire area of the back panel. The back panel 126, defines a back panel edge 127, a back panel crotch edge 175, a back panel first side edge 128, and a back panel second side edge 129. The back panel first side edge 128 is opposed to the back panel second side edge 129 in the transverse direction 33. The back panel 126 defines a back panel width 176 measured, with the garment fully extended, in the transverse direction 33 between the back panel first side edge 128 and the back panel second side edge 129. The back panel 126 also defines a back panel length measured, with the garment fully extended, in the longitudinal direction 32 between the back panel edge 127 and the back panel crotch edge 175.

The crotch region 30 may also be defined, at least in part, by an insert panel 101. The insert panel 101 may be an elastic laminate like any of those described herein. However, in some embodiments, the insert panel 101 may be primarily non-elastic. The insert panel 101 is disposed longitudinally between and interconnects the front panel 122 and the back panel 126. In some embodiments, the insert panel includes a body-facing liner 37, a garment-facing back sheet 38, and an absorbent member 36 positioned between the liner 37 and the back sheet 38 as illustrated in FIGS. 1 and 2. In various embodiments, the body-facing liner 37 may be partially or completely liquid-permeable and the back sheet 38 may be partially or completely liquid-impermeable. The absorbent member 36 may extend in the longitudinal direction 32 from the front panel 122 to the back panel 126 as illustrated or may only extend to the front panel or may only extend to the back panel (not illustrated). The insert panel 101 defines an insert panel width 102 measured, with the garment fully extended, in the transverse direction 33 between an insert panel first sided edge 103 and an insert panel second side edge 104. The insert panel width 102 defines an insert panel maximum width 105 and an insert panel minimum width 106. In some embodiments, the insert panel minimum width 106 is less than 75% the insert panel maximum width 105. The insert panel 101 also defines an insert panel front edge 107 and an insert panel back edge 108.

In embodiments having a front panel 122, a back panel 126 and an insert panel 101, the product length 58 is measured from the front panel edge 123 to the back panel edge 127 with the absorbent garment 20 fully extended in the longitudinal direction 32. In these embodiments, the front panel width 172 and the back panel width 176 are measured with the absorbent garment 20 fully extended in the transverse direction 33. Also in these embodiments, and as representatively illustrated in FIG. 5, the front panel first side edge 124 may be connected to the back panel first side edge 128 at the first side seam 74 and the front panel second side edge 125 may be connected to the back panel second side edge 129 at the second side seam 75, such that the garment defines a pull-on, pant-like configuration having a waist opening 50 and two leg openings 51.

As illustrated, a portion of the absorbent member 36 longitudinally overlaps a portion of the laminate 39 of the front region 22 or the front panel 122 to define in the laminate 39 an overlapped region 44 and a non-overlapped region 46. At least a portion of the overlapped region 44 of the laminate 39 is non-elastomeric, and at least a portion of the non-overlapped region 46 of the laminate 39 is elastomeric. In one preferred approach, the entire laminate 39 is constructed of an elastomeric film laminate which includes an elastomeric film layer and at least one nonwoven facing layer, and a portion of the laminate has been "deactivated" or "deadened" to render it non-elastomeric. In another preferred approach, the entire laminate is constructed of an elastomeric laminate which includes elastomeric threads or fibers and at least one nonwoven facing layer, and a portion of the laminate has been "deactivated" or "deadened" to render it non-elastomeric. As used herein, "elastomeric" refers to a material or composite which can be elongated by at least 50 percent of its relaxed length and which will recover, upon release of the applied force, at least 50 percent of its elongation. It is generally preferred that the elastomeric material or composite be capable of being elongated by at least 100 percent, more preferably by at least 200 percent, of its relaxed length and recover, upon release of an applied force, at least 50 percent of its elongation. "Non-elastomeric" refers to a material or composite that is non-extensible, or that is extensible but will recover no more than 20 percent of its elongated length after release of an applied elongating force. "Non-extensible" refers to a material that cannot stretch or extend by more than 25 percent of its relaxed length without fracture upon application of a biasing force. "Partially elastomeric" refers to a material or composite which can be elongated by at least 50 percent of its relaxed length and which will recover, upon release of the applied force, more than 20 percent but less than 50 percent of its elongation.

In particular embodiments, the majority of the overlapped region 44 of the laminate 39 is non-elastomeric. In particular embodiments, the entirety of the overlapped region 44 of the laminate 39 is non-elastomeric. In some embodiments, the non-elastomeric region 48 may be larger than the overlapped portion of the absorbent member 36. The relatively larger non-elastomeric region 48 (larger relative to the overlapped region 44) can assist in minimizing the amount of retraction/bunching directly around the periphery or partial periphery of the absorbent member 36, which can, in certain desirable embodiments, provide a smoother, "flatter," more underwear-like garment.

In particular embodiments, the majority of the overlapped region 44 of the laminate 39 is only partially-elastomeric. In particular embodiments, the entirety of the overlapped region 44 of the laminate 39 is only partially-elastomeric. In particular embodiments, substantially the entirety of the area of the overlapped region has an elasticity of less than half, less than a quarter, or less than a tenth of the elasticity of substantially the entirety of the area of the non-overlapped portion.

In particular embodiments, the majority of the non-overlapped region 46 of the laminate is elastomeric; that is, more than 50% of the area of the non-overlapped region of the laminate is elastomeric. In preferable embodiments, more than 75%, and still more preferably more than 90% of the area of the non-overlapped region of the laminate is elastomeric. In particular embodiments, the entirety of the non-overlapped region of the laminate is elastomeric. For example, as representatively illustrated in FIG. 1, the entirety of the non-overlapped region 46 of the laminate 39 is elastomeric.

In particular embodiments, substantially the entirety of the area of the non-overlapped region 46 has an elasticity of more than twice, more preferably of more than three times, and still more preferably more than four times the elasticity of substantially the entirety of the area of the overlapped portion 44. In particular embodiments, elastomeric regions of the laminate are elastomeric in both the transverse direction and the longitudinal direction. In other embodiments, elastomeric regions of the laminate are elastomeric only in the transverse direction.

In particular embodiments, the back region 26, too, is constructed at least in part of a laminate 39 that comprises a polymeric film layer 40 and a nonwoven layer 41, wherein both the polymeric film layer 40 and the nonwoven layer 41 extend substantially throughout the entire area of the laminate 39. The back region 26 can include any of the features or configurations described above with respect to the front region 22 (for example, with respect to the composition of the laminate, or regarding the elasticity or non-elasticity of the overlapped or non-overlapped regions). Furthermore, both the front and back regions of the garment can simultaneously feature any of the features or configurations described above with respect to the front region 22, alone or in combination.

Referring to FIG. 2, optional containment flaps are illustrated. The first containment flap 63 and the second containment flap 64 may extend in the longitudinal direction 32 and may be attached to a body-facing surface 66 of the front region 22 and/or the crotch region 30 and/or the back region 26. The containment flaps 63 and 64 of FIG. 1 are attached in the front region 22, the crotch region 30, and the back region 26. In some embodiments, the containment flaps 63 and 64 are attached to the body-facing surface 66 of an insert panel 101 as illustrated in FIG. 1. In these embodiments, the containment flaps 63 and 64 may extend in the longitudinal direction 32 from the insert panel front edge 107 to the insert panel back edge 108. In these embodiments, the containment flaps 63 and 64 may terminate at the insert panel front edge 107 and may terminate at the insert panel back edge 108 as illustrated in FIG. 1. In other embodiments, the containment flaps may extend from the front edge to the back edge of the absorbent garment (not illustrated).

Each containment flap 63 and 64 defines a flap height 65 measured, in a direction perpendicular to both the longitudinal direction and the transverse direction, from an attachment edge 69 to a distal edge 68. In various embodiments, the flap height 65 may be less than 20 mm, less than 18 mm, or less than 15 mm. The attachment edges 69 of the containment flaps 63 and 64 have a flap spacing 70 as measured in the transverse direction 33 as illustrated in FIG. 2. In various embodiments, the flap spacing 70 may be 80 to 140 mm, 90 to 120 mm, or 95 to 105 mm. In some embodiments, the flap spacing 70 may be at least 90 mm. In some embodiments, the flap spacing 70 may be about 102 mm. Each containment flap may also be spaced apart (off-set) from the absorbent member side edges. For example, the first containment flap 63 may have a flap off-set 71 from the absorbent member first side edge 84 as illustrated in FIG. 2. Likewise, the second containment flap 64 may have a flap off-set 71 from the absorbent member second side edge 85 as illustrated in FIG. 2. In various embodiments, the flap off-set 71 may be at least 10 mm, at least 20 mm, at least 30 mm, or at least 40 mm. In some embodiments, the flap off-set may be 10 to 40 mm, 15 to 30 mm, about 20 mm, or about 25 mm. The containment flaps can include one or more elastic members (not illustrated) proximate the distal edge 68 and/or proximate the attachment edge 69.

Referring to FIG. 5, in particular embodiments, an optional elastomeric waistband 60 may be attached to or formed from the front region 22 and/or attached to or formed from the back region 26. Such waistbands are preferably but not necessarily elastomeric, and can comprise elastomeric films, elastomeric strands or ribbons, elastomeric foams, elastomeric laminates, or the like.

The present invention provides absorbent garments having a relatively thin and narrow design through the crotch to provide improved comfort and close fit while maintaining necessary containment and capacity. It has been found that narrowing the absorbent member and increasing the absorbent member thickness in the crotch does not adequately address comfort and fit. Additionally, it has been found that narrowing the absorbent member while maintaining product thickness helps improve comfort but the containment and capacity performance of the product may suffer. Specifically, narrowing the absorbent insert at the crotch by removing absorbent material can result in inadequate quantity of absorbent material to capture liquids before a leak occurs. The present inventors have found that careful design of the width of the absorbent member at the crotch relative to the minimum width of the absorbent garment can provide the comfort, fit, and performance desired. Information regarding two exemplary embodiments of the present invention is included in Table 1 below. Additionally, Table 1 includes other commercially available products for comparison.

In general, the minimum width of the absorbent member is positioned in the crotch region of the absorbent garment. However, it has been found that the minimum crotch width relative to the width of the absorbent member at the crotch is critical to product performance, comfort, and fit. Specifically, it has been found that the absorbent member minimum width should be less than 53% of the minimum crotch width of the chassis to achieve an adequate "bucket" to retain large amounts of urine until the absorbent member can absorb the fluid. The larger bucket design helps compensate for the reduction of absorbent material in the crotch and provides extra time for the absorbent member to absorb without leaking by wicking fluid from the portion of the absorbent member having the minimum width (crotch) to the portion of the absorbent member having the maximum width (ears).

It has also been found that a highly shaped absorbent member can be advantageous in providing an absorbent garment with close to the body fit while maintaining good product performance. A highly shaped absorbent member has a relatively narrow width at the crotch region as compared with the width in the absorbent member ears. The narrow width of the absorbent near the crotch helps provide comfort to the user while the wider width of the absorbent near the ears helps provide the absorbent capacity needed. The improved bucket design works in combination with the highly shaped absorbent member by retaining body fluid at the point of insult while the absorbent member absorbs and wicks fluid to other areas of the absorbent member, like the ears.

It has also been found that a highly shaped chassis can be advantageous in providing an absorbent garment with close to the body fit, comfort, and good product performance. This is particularly applicable to absorbent garments adapted for use by adults. A highly shaped chassis has a relatively narrow width at the crotch region as compared with the width in front and back regions to help minimize bulk between the legs while still providing maximum coverage and fit around the hips, buttocks, and belly.

In optional embodiments, the absorbent article may include containment flaps. It has been found that the narrow crotch region of the present invention in combination with relatively short containment flaps provides good product performance. It has also been found that the narrow crotch region of the present invention in combination with widely spaced flaps relative to the absorbent member minimum width provides good product performance. It is believed that shorter containment flaps work in cooperation with the improved bucket design of the present invention because should the containment flaps be compressed or folded over, the relatively short height minimizes the amount of fluid blocked from reaching the target zone of the absorbent member. However, the shorter flaps provide adequate containment when used in conjunction with the "bucket" configuration of the present invention.

TABLE 1

| | Absorbent Member Min. Width (mm) | Minimum Crotch Width (mm) | Front/Back Region Width (mm) | Absorbent Member Max. Width (mm) | Product Length (mm) | Flap Height (mm) | Flap Spacing (mm) | Flap Offset (mm) | Intake Layer Min. Width (mm) | Bucket Ratio | Absorbent Shape Ratio | Chassis Shape Ratio |
|---|---|---|---|---|---|---|---|---|---|---|---|---|
| Tena for Women, S/M (Film laminate) | 85 | 130 | 630 | 120 F 135 B | 720 | n/a | n/a | n/a | 55 | 0.65 | 0.71 0.63 | 0.21 |
| Certainty (Walgreens) for Women, S/M (Film laminate) | 100 | 175 | 615 | 100 | 715 | n/a | n/a | n/a | 83 | 0.57 | 1.0 | 0.28 |
| Certainty (Walgreens) for Women, S/M (Stranded Laminate) | 100 | 200 | 660 | 100 | 720 | n/a | n/a | n/a | 82 | 0.5 | 1.0 | 0.30 |
| Compose | 105 | 225 | 700 | 160 | 795 | n/a | n/a | n/a | 80 | 0.47 | 0.66 | 0.32 |
| FitRight, Size Large | 115 | 190 | 745 | 115 | 820 | 32 | 135 | 10 | 75 | 0.61 | 1.0 | 0.26 |
| KAO Relief, Size Large, Japan | 115 | 290 | 1260 | 250 | 780 | 25 | 245 | 65 | n/a | 0.39 | 0.46 | 0.23 |
| Abena Abriflex Premium, Air Plus, Japan, Size M/L2 | 90 | 160 | 740 | 185 F 200 B | 770 | 15 | 160 | 35 | n/a | 0.56 | 0.49 0.45 | 0.22 |

TABLE 1-continued

| | Absorbent Member Min. Width (mm) | Minimum Crotch Width (mm) | Front/Back Region Width (mm) | Absorbent Member Max. Width (mm) | Product Length (mm) | Flap Height (mm) | Flap Spacing (mm) | Flap Offset (mm) | Intake Layer Min. Width (mm) | Bucket Ratio | Absorbent Shape Ratio | Chassis Shape Ratio |
|---|---|---|---|---|---|---|---|---|---|---|---|---|
| Shopko Training Pant, Mabe SA | 85 | 170 | 345 | 85 | 480 | 35 | 105 | 10 | 80 | 0.5 | 1.0 | 0.49 |
| Toys R Us Training Pant, AHP U.S. | 80 | 155 | 345 | 80 | 500 | 40 | 120 | 20 | 70 | 0.52 | 1.0 | 0.45 |
| Kotex Personals Protective Panties, Size 8/9/10, U.S. | 105 | 105 | 595 | 155 | 800 | n/a | n/a | n/a | n/a | 1.0 | 0.68 | 0.18 |
| Depend Underwear-Female moderate and max-Small/Medium | 106 | 149 | 749 | 170 | 740 | n/a | n/a | n/a | 62 | 0.71 | 0.62 | 0.20 |
| Depend Silhouette S/M, Female Max, U.S. | 95 | 149 | 749 | 178 | 735 | n/a | n/a | n/a | 83 | 0.64 | 0.53 | 0.20 |
| Depend Real Fit, Male, Max, U.S. | 95 | 210 | 749 | 178 | 718 | n/a | n/a | n/a | 83 | 0.45 | 0.53 | 0.28 |
| Depend Adjustable Underwear, Max, S/M, U.S. | 114 | 221 | 749 | 170 | 781 | n/a | n/a | n/a | 62 | 0.52 | 0.67 | 0.30 |
| Depend Active Fit Underwear, Female, S/M, Moderate, U.S. | 62 | 149 | 749 | 100 | 665 | n/a | n/a | n/a | 49 | 0.42 | 0.62 | 0.20 |
| Embodiment 1 | 62 | 149 | 750 or 840 | 150 | 690 | 13 | 112 | 25 | 49 | 0.42 | 0.41 | 0.20 or 0.18 |
| Embodiment 2 | 62 | 210 | 750 or 840 | 150 | 718 | 20 | 112 | 25 | 49 | 0.3 | 0.41 | 0.28 or 0.25 |

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. An absorbent garment defining a longitudinal direction and a transverse direction, the absorbent garment comprising,
    a front region comprising a front panel defining a front panel edge, a front panel crotch edge, a first front panel side edge, and a second front panel side edge transversely opposed to the first front panel side edge, wherein the front panel defines a front panel width in the transverse direction between the first front panel side edge and the second front panel side edge, wherein the front panel defines a front panel length in the longitudinal direction between the front panel edge and the front panel crotch edge, wherein the front panel width and the front panel length define a front panel area, the front panel comprising a laminate of two nonwoven layers superposed on opposing surfaces of a polymeric film layer, wherein the two nonwoven layers and the polymeric film layer extend substantially through the entire front panel area;
    a back region comprising a back panel defining a back panel edge, a back panel crotch edge, a first back panel side edge, and a second back panel side edge transversely opposed to the first back panel side edge, wherein the back panel defines a back panel width in the transverse direction between the first back panel side edge and the second back panel side edge, wherein the back panel defines a back panel length in the longitudinal direction between the back panel edge and the back panel crotch edge, wherein the back panel width and the back panel length defines a back panel area, the back panel comprising a laminate of two nonwoven layers superposed on opposing surfaces of a polymeric film layer, wherein the two nonwoven layers and the polymeric film layer extend substantially through the entire back panel area, wherein the back panel of the back region is separate from and spaced apart from, in the longitudinal direction, the front panel of the front region;
    a crotch region comprising an insert panel, wherein the insert panel is separate from each of the front panel and the back panel, disposed in the longitudinal direction between and interconnecting the front panel of the front region and the back panel of the back region, wherein the insert panel defines a minimum crotch width,
    wherein the minimum crotch width is less than 30% the front panel width, and wherein the absorbent garment defines a product length, as measured in the longitudinal direction between the front panel edge and the back panel edge, of at least 600 mm;
    wherein the insert panel comprises an absorbent member positioned between a liquid-permeable body-facing liner and a liquid-impermeable garment facing backsheet, wherein the absorbent member defines an absorbent member width measured transversely between an absorbent member first side edge and an absorbent member second side edge, the absorbent member width defining an absorbent member maximum width and an absorbent member minimum width, wherein the absorbent member minimum width is less than 80 mm, the absorbent member minimum width is less than 60% the absorbent member maximum width, the absorbent member minimum width is less than 53% the minimum crotch width, and the absorbent garment defines an absorbent capacity of at least 600 g; and the first front panel side edge is connected to the first back panel side edge at a first side seam and the second front panel side edge is connected to the second back panel side edge at a second side seam to form a pant-like configuration having a waist opening and two leg openings.

2. The absorbent garment of claim 1, further comprising, a first and a second containment flap extending in the longitudinal direction and being joined to a body-facing surface of the absorbent garment, wherein each of the first and the second containment flap defines a height, measured from an attachment edge to a distal edge, of less than 20 mm.

3. The absorbent garment of claim 2, wherein the absorbent member minimum width is less than 65 mm and each of the first and the second containment flaps have an off-set of at least 10 mm relative to the absorbent member minimum width.

* * * * *